(12) United States Patent
Mercier et al.

(10) Patent No.: US 7,563,435 B2
(45) Date of Patent: *Jul. 21, 2009

(54) TRANSPARENT LIP TREATMENT GEL

(75) Inventors: Michel F. Mercier, Mountainside, NJ (US); Paul Thau, Berkeley Heights, NJ (US); John Chase, Bedminster, NJ (US)

(73) Assignee: MMP, Inc., South Plainfield, NJ (US)

( * ) Notice: Subject to any disclaimer, the term of this patent is extended or adjusted under 35 U.S.C. 154(b) by 796 days.

This patent is subject to a terminal disclaimer.

(21) Appl. No.: 10/948,993

(22) Filed: Sep. 24, 2004

(65) Prior Publication Data

US 2005/0100569 A1   May 12, 2005

Related U.S. Application Data

(63) Continuation-in-part of application No. 10/282,821, filed on Oct. 28, 2002, now Pat. No. 7,488,471.

(51) Int. Cl.
*A61Q 1/04* (2006.01)
*A61Q 1/06* (2006.01)

(52) U.S. Cl. .................................. 424/64; 424/401
(58) Field of Classification Search .............. None
See application file for complete search history.

(56) References Cited

U.S. PATENT DOCUMENTS 5,922,311 A * 7/1999 Terren et al. ............. 424/70.12
7,262,158 B1 * 8/2007 Lukenbach et al. ......... 510/122

* cited by examiner

*Primary Examiner*—Jyothsna A Venkat
(74) *Attorney, Agent, or Firm*—Louis C. Paul

(57) ABSTRACT

The present invention relates to transparent or clear emulsions for cosmetic or pharmaceutical use that are suitable for application to the human lips and to the facial area around the lips. The transparent emulsions of the present invention comprise an oil phase, containing at least one lipophilic solvent; an aqueous phase; and an emulsifying system containing at least one non-ethoxylated fatty acid ester emulsifier having a hydrophilic-lipophilic balance ("HLB") from about 11 to about 16. Preferred non-ethoxylated fatty acid ester emulsifiers are sucrose esters, in particular sucrose palmitate and sucrose laurate.

12 Claims, No Drawings

TRANSPARENT LIP TREATMENT GEL

CROSS-REFERENCE TO RELATED APPLICATIONS

This is a continuation in part of U.S. patent application Ser. No. 10/282,821, filed Oct. 28, 2002, now U.S. Pat. No. 7,488,471 and claims priority to that application.

STATEMENT REGARDING FEDERALLY-SPONSORED RESEARCH OR DEVELOPMENT

Not Applicable.

FIELD OF THE INVENTION

The field of invention of the present invention relates to transparent or clear gel emulsions for use in cosmetic, personal care or cosmeceutical compositions. The invention particularly relates to transparent or clear gel emulsions suitable for application to the human lips and to the facial area around the lips.

BACKGROUND OF THE INVENTION

Emulsions are formed from at least two liquid phases, typically oil and water that are immiscible in each other. In an oil-in-water emulsion, for example, the oil phase is comprised of ingredients that are substantially insoluble in water. In this type of emulsion, the oil phase is composed of droplets that are finely dispersed in the water phase. It is therefore referred to as the inner or discontinuous phase, while the water phase is referred to as the outer or continuous phase. Conversely, in a water-in-oil emulsion, the water phase is finely dispersed in the oil phase and is referred to as the inner, discontinuous, phase, while the oil phase is the outer, continuous phase. Emulsions are inherently unstable and tend to separate into their constituent phases. Emulsions must therefore include emulsifiers that help create and maintain the uniform fine dispersion of the inner phase in the outer phase, and retard or prevent coalescence of the droplets and eventual separation of the emulsion into its constituent phases.

Emulsions—both water-in-oil and oil-in-water—are typically opaque (i.e., white or pale yellow in color). Transparent emulsion systems were described, in theory, as early as the 1940s. In those systems, in order to achieve transparency, the refractive indexes of the oil and water phases had to be matched prior to formation of the emulsion. See, e.g., Clayton, Theory of Emulsions, page 153 ($4^{th}$ Edition, 1943). Although they had been described in the 1940's, transparent emulsion systems of this type did not become commercially available until much later.

Transparent emulsions first became commercially available in the early 1960s. However, these emulsions did not achieve their transparency by matching refractive indexes. Rather, a transparent appearance was achieved by making the size of the dispersed droplets small enough (i.e., less than about 0.08 microns) so as to be unresolvable by visible light. Such emulsions are known as microemulsions. See, e.g., Gallagher, "Microemulsion Gels: A Formulator's Guide," Happi (February 1993). Microemulsions typically required a high content (i.e., 15-20%) of high hydrophilic-lipophilic balance ("HLB") non-ionic ethoxylated emulsifiers. Illustrative are Score™ and Clean and Groom™ hair dressings. See, e.g., U.S. Pat. No. 3,101,300. Because non-ionic ethoxylated emulsifiers are defatting and irritating to the skin when used at high levels, products containing them were viewed as unacceptable for topical application to the skin for an extended period of time. At least one previous attempt to formulate a clear microemulsion gel without the use of ethoxylated emulsifiers was unsuccessful. Gallagher described such an ethoxylated emulsifier-free microemulsion gel as not stable, having a very high set point, becoming clouded upon aging. Gallagher, supra.

By the early 1980s—with the availability of cyclomethicone and the introduction of specialty water-in-silicone emulsifiers (e.g. dimethicone copolyols) as raw materials —the development of transparent water-in-oil emulsions that were not microemulsions and that achieved their transparency by matching the refractive indexes of the oil and water phase became commercially possible. See, e.g., Dow Corning, "Using Silicone Formulation Aids to Formulate Cosmetic Systems: Quick Start Guide" (1995). Such transparent water-in-oil emulsions had several drawbacks. For example, they have the drawbacks typically associated with water-in-oil emulsions in general, such as delayed bioavailability of water-soluble active ingredients. Because such active ingredients are in the inner phase they can only become bioavailable after the emulsion breaks down. In addition, it is difficult to make refractive index adjustments at the end of processing. Therefore, in order to achieve transparency, the refractive indexes of the oil and water phases of these transparent water-in-oil emulsions had to be matched before combining the two phases.

Transparent oil-in-water emulsions of the present invention overcome the above limitations. First, they have the advantageous characteristics typical of oil-in-water emulsions. Thus, for example, water-soluble active ingredients can be easily added to the aqueous phase and are bioavailable at, or shortly after, application. In addition the refractive index of the aqueous phase can be readily adjusted (e.g., by adding water to adjust the refractive index downward, or by adding glycerin or propylene glycol to adjust the refractive index upward) after the emulsion has been formed to match the refractive index of the oil phase. It is therefore not necessary to perfectly match the refractive indexes of the two phases before formation of the emulsion.

While some transparent oil-in-water emulsions have been described in the prior art, such emulsions generally contain ethoxylated emulsifiers and have a tendency to dry the skin. Furthermore, they generally require more vigorous mixing and are more viscous so that they tend to trap bubbles, which are difficult to remove and which negatively affect the clarity of the final product. Thus, there is a need for transparent oil-in-water emulsions that are not only milder to the skin, but also easier to process.

The term "transparent lip treatment gel" shall mean a transparent oil-in water emulsion gel compositions of the present invention that are suitable for application to the lips of a user and the facial area around the lips, including cosmetic products such as lip glosses, lip balms and the like.

As part of the aging process, fine lines and wrinkles develop on or around the lip area. In part, this is caused by exposure to pollutants and ultraviolet radiation. Transparent lip treatment gels of the present invention provide a protective barrier against such damaging environmental agents. Sunscreens and antioxidants can be incorporated to transparent lip treatment gels of the present invention, thereby preventing DNA and cellular damage that are associated with aging. In addition, by incorporating anti-wrinkle and anti-aging ingredients, including, for example, short-chain polypeptides, dermatologic agents, vitamins, emollients and moisturizers, and mixtures thereof, transparent lip treatment gels of the present invention can also help reduce the appearance of fine lines and wrinkles on or around the lip area, thereby imparting a smoother and more full (or plump) appearance.

SUMMARY OF THE INVENTION

The invention is a novel transparent or clear oil-in-water emulsion that comprises an oil phase containing at least one lipophilic solvent; an aqueous phase; and an emulsifying system containing at least one non-ethoxylated fatty acid ester having an HLB from about 11 to about 16. The refractive indexes of the aqueous and oil phases of the emulsion are matched so that the resulting emulsion is essentially transparent or clear. The refractive index of the aqueous phase is about +/−0.003 to about +/−0.007 of that of the oil phase, preferably about or less than +/−0.005. Optionally, a polymeric additive may be incorporated into the aqueous phase of the emulsion to create an emulsion gel of varying viscosities depending on the amount and type of polymer used. The emulsion of the present invention is suitable for application to the human lips and the facial area around the lips.

BRIEF DESCRIPTION OF THE DRAWINGS

Not applicable.

DETAILED DESCRIPTION OF INVENTION

The transparent oil-in-water emulsion of the present invention is suitable for application to the human lips and the facial area around the lips. The novel transparent or clear oil-in-water emulsion comprises an oil phase containing at least one lipophilic solvent; an aqueous phase; and an emulsifying system containing at least one non-ethoxylated fatty acid ester having an HLB from about 11 to about 16. The refractive indexes of the aqueous and oil phases of the emulsion are matched so that the resulting emulsion is essentially transparent or clear. The refractive index of the aqueous phase is about +/−0.003 to about +/−0.007 of that of the oil phase, preferably about or less than +/−0.005. Optionally, a polymeric additive may be incorporated into the aqueous phase of the emulsion to create an emulsion gel of varying viscosities depending on the amount and type of polymer used.

The oil-in-water emulsions of the present invention are exceptionally mild. This is not only because the emulsifiers used in the present invention are exceptionally mild and considerably less irritating to the skin and eyes than ethoxylated emulsifiers, but also because surprisingly the level necessary to stabilize the emulsions (and thus the total level of total emulsifier present) has been found to be very low. Indeed, surprisingly sucrose esters alone can stabilize the emulsions of the invention. The oil-in-water emulsions of the present invention surprisingly have also been found to have skin moisturizing properties.

In addition to their mild and hydrating characteristics, the emulsions of the present invention are also more conveniently processed. In order to achieve transparency in an emulsion, it is important that air bubbles be eliminated or essentially minimized from the emulsion. Prior art emulsions, in particular those containing ethoxylated emulsifiers, required high shear mixing which tends to entrap small bubbles. Since removal of smaller bubbles is difficult, those bubbles often remain in the final products, thereby decreasing clarity and transparency. In contrast, it has been surprisingly found that transparent oil-in-water emulsions of the present invention may be formed by medium energy loop mixing. Bubbles produced during this lower energy process tend to be bigger and rise to the surface of the emulsion (where they burst), thus resulting in an essentially bubble-free emulsion. Furthermore, since a stable emulsion according to the present invention can be formed with low levels of sucrose esters, the resulting base emulsion is relatively more flowable than prior art emulsions which required a larger concentration of surfactant, and thus tend to be more viscous. Whereas bubbles become entrapped in the more viscous prior art base emulsions, the more flowable emulsions of the present invention allow bubbles to rise and dissipate, producing an aesthetically acceptable transparent base emulsion. The increased flowability of the emulsions of the present invention is also advantageous because the viscosity and consistency of the emulsion may be adjusted within a relatively wide range after formation of the emulsion by the addition of polymeric additives in the quantity and type necessary to achieve the desired characteristics. Furthermore, this is accomplished on an essentially bubble-free base emulsion. In contrast, the addition of polymeric thickeners to prior art emulsions tends to further entrap smaller bubbles already present.

The oil phase of the present invention comprises at least one lipophilic solvent and preferably other lipophilic cosmetic or pharmaceutically useful ingredients known to those of ordinary skill in the art. Preferably the lipophilic solvent is selected from the group consisting of volatile silicone fluids, non-volatile silicone fluids, high molecular weight silicone polymers in the range from about 60,000 centistokes to about 1,000,000 centistokes, liquid fatty alcohols from 16 to 22 carbon atoms per molecule, volatile hydrocarbon fluids and vegetable oils. Preferred volatile silicone fluids that can be used in the oil phase of the present invention include cyclomethicone (i.e., cyclopentasiloxane and cyclohexasiloxane) and dimethicone (0.65 centistokes). A preferred volatile hydrocarbon fluid usable in the present invention is isododecane, sold under the tradename Permethyl 99A, by Presperse Inc., Piscataway, N.J. The oil phase may further comprise a lipophilic co-solvent selected from the group consisting of fatty acid esters, liquid branched chain fatty alcohols from 16 to 20 carbon atoms in length, and triglycerides. A preferred triglyceride is caprylic/capric triglyceride. To improve feel, dimethicone/vinyl dimethicone cross polymer may be added to the oil phase. The oil phase comprises from about 30% to about 70% by weight of the emulsion, preferably from about 40% to about 50%. In order to aid in matching refractive indexes of the aqueous and oil phases, the oil phase may include index adjusting agents known to those of ordinary skill in the art such as halogenated solvents.

The aqueous phase of the present invention comprises water and preferably other water-soluble cosmetically or pharmaceutically useful ingredients known to those of ordinary skill in the art. In order to aid in matching the refractive indexes of the aqueous and oil phases, the aqueous preferably includes one or more polyols selected from the group consisting of glycerin, polyethylene glycol, propylene glycol, polypropylene glycol, 1,3 butylene glycol, methylpropanediol, hexylene glycol and sorbitol. Preferably the polyol has a molecular weight from about 75 to about 10,000 daltons, more preferably from about 200 to about 5000 daltons, and most preferably from about 300 to about 1000 daltons. A preferred polyol for use in the present invention is polyethylene glycol 400, sold under the tradename Carbowax PEG 400 by Union Carbide, Houston, Tex., alone or in combination with glycerin. Preferably, the polyol is present in an amount of from about 10% to about 35% of the total composition, more preferably from about 15% to about 30% of the total composition, and most preferably it makes up from about 18% to about 25% of the total composition. Alternatively to the polyol, the aqueous phase of the emulsion may contain polysaccharides or other agents known to those of ordinary skill in the art to be useful in adjusting the refractive index of the aqueous phase.

The emulsifying system includes at least one non-ethoxylated fatty acid ester emulsifier having an HLB from about 11 to about 16, preferably from about 13 to about 16. Preferably the emulsifier is a sucrose ester. More preferably the sucrose ester emulsifier is selected from the group consisting of sucrose laurate, sucrose stearate, sucrose palmitate, sucrose oleate, sucrose myristate, sucrose cocoate and sucrose isostearate, or a combination thereof. Most preferably the non-ethoxylated emulsifier is a sucrose laurate or a sucrose palmitate. Preferably the percentage of the non-ethoxylated fatty acid ester is less than 5% by weight of the total composition, more preferably less than 3% by weight of the total composition, and most preferably less than 1.5%. When the non-ethoxylated fatty acid ester is a sucrose ester, the preferred range is from about 0.5 to 5% by weight of the total composition, and more preferably from about 1 to about 2.5% by weight of the total composition, and most preferably less than 1.5% of the total composition.

Optionally, a polymeric additive may be incorporated into the aqueous phase of the emulsion in order to achieve a desired viscosity or gel consistency. The polymeric additive is a water-soluble polymer selected from the group consisting of sclerotium gum, xanthan gum, sodium alginate, carbomer, cellulose ethers and acrylate polymers. Sclerotium gum is sold under the tradename Clearogel CS11D by MMP, Inc., South Plainfield, N.J. Acrylate polymers usable in the present invention include: steareth-20 methylacrylate copolymer, sold under the tradename Aculyn 22 by Rohm & Haas Company, Philadelphia, Pa.; Pemulen TR-1 and TR-2 ($C_{10}$-$C_{30}$ alkyl acrylate crosspolymer), both sold by Goodrich Specialty Chemicals, Cleveland, Ohio; and Hypan QT1000 and SA100H, both acrylonitrogen copolymers, sold by Lipo Chemicals, Inc., Patterson, N.J. Preferred polymers for use in the present invention are Clearogel CS11D and Aculyn 22. Depending upon the viscosity to be achieved, the amount of polymeric additive can range from about 0.1% to about 2.5% by weight of the total composition, preferably 0.5% to 0.75% by weight of the total composition. In general, the greater the amount of the polymeric additive, the greater the viscosity.

In order to produce the desired products, the basic components of the invention as described above may be combined with other cosmetic and pharmaceutical ingredients which are well-known to cosmetic and pharmaceutical chemists. Examples of such additional components include, but are not limited to, antioxidants, anti-wrinkle agents, vitamins, sunscreen actives, moisturizers, as well as purely cosmetic ingredients, such as pigments, colorants, water-soluble emollients, humectants, stabilizers and fragrances. Sunscreen actives are organic or inorganic agents that absorb or reflect light waves over a specified spectrum, thus preventing potentially harmful erythemal ultraviolet radiation from reaching and damaging the skin.

The transparent oil-in-water gel emulsion of the present invention is prepared according to principles and techniques generally known to those skilled in the cosmetic and pharmaceutical arts. As described below, a base emulsion comprising the oil and water phases and non-ethoxylated fatty acid ester emulsifier is prepared. A polymeric thickener is optionally added to the base emulsion when increased viscosity is desired. Finally, refractive indexes of the oil and water phases are matched. More particularly, ingredients which are miscible or soluble in the water phase are combined with the non-ethoxylated fatty acid ester emulsifier using a loop blade mixer at medium speed (i.e., from about 200 to about 250 rotations per minute) in a main vessel. Air bubbles, if any, are removed from the aqueous phase by slow mixing with a loop blade mixer (i.e., from about 60 to about 100 rotations per minute). Oil phase ingredients are combined in a separate vessel. After the refractive indexes of the oil and water phases are matched to one another using the polyols described above or other techniques and materials known to those of ordinary skill in the art, the oil phase is gradually added to the main vessel. The two phases are combined and emulsified by gradually increasing the speed of the loop mixer from slow to medium as described above. Next, polymeric thickeners are added. Lastly, final adjustments to match the refractive indexes are made (e.g., by adding water to adjust the refractive index downward, or by adding glycerin or propylene glycol to adjust the refractive index upward).

The invention is further illustrated by the following examples, which are intended to illustrate and not limit the invention.

EXAMPLE 1

Transparent Lip Treatment Gel

An SPF 15 transparent lip treatment gel with a pH of 7.41 and a viscosity of 164,000 cps. (LV4@3 rpm) was made according to the procedure set forth below. The gel was stable at 40° C. for six weeks, at room temperature for six weeks, and after three freeze/thaw cycles.

| Tradename | INCI Name | % wt/wt |
|---|---|---|
| Phase A | | |
| DI Water | Water | 20.55 |
| Disodium EDTA | Disodium EDTA | 0.10 |
| Glycerin 99.5% | Glycerin | 10.00 |
| Polycast ™ 3 (MMP) | Polyglycerin | 17.00 |
| Sisterna ® L70-C (MMP) | Sucrose Laurate | 3.00 |
| Clearogel ™ CS11D (MMP) | Scleroglucan | 0.10 |
| Phase B | | |
| Clearocast ™ 550 (MMP) | Isononyl Isononanoate and Isododecane | 10.00 |
| Dimethicone (6 cst.) | Dimethicone | 10.00 |
| Parsol MCX | Ethylhexyl Methoxycinnamate | 7.50 |
| Neoheliopan OS | Ethylhexyl Salicylate | 5.00 |
| Clearocast ™ 100 (MMP) | Dimethicone | 15.00 |
| Phase C | | |
| Aculyn 22 | Acrylates/Steareth-20 Methacrylate Copolymer | 1.25 |
| Phase D | | |
| TEA 99% | Triethanolamine | 0.50 |

Phase A was prepared as follows: In main vessel combine water and Disodium EDTA. In a side vessel, a prepare slurry of Glycerin and Clearogel CS11D. Add the slurry to the main vessel with medium loop mixing. Start heating to 65° C., hold for 10 minutes. Start cooling to 25° C. Add Polycast™ 3 to the main vessel, mix thoroughly. Add Sucrose Laurate and continue mixing until all ingredients are in solution. Measure refractive index of Phase A. If necessary, adjust refractive index to 1.427+/−0.005. Refractive index can be lowered by adding water or elevated by adding glycerin.

Phase B was prepared in a separate vessel by combining Parsol MCX, Neoheliopan OS, Clearocast 100, Dimethicone (6 cst.) and Clearocast 550 in a separate vessel. (Phase B should appear clear and have a refractive index of about 1.427+/−0.005.) Using slow loop mixing Phase B is added to Phase A in the main vessel. The speed of the slow loop mixing may be increased gradually so as not to incorporate air. After Phases A and B are combined, Phase C is added to the main vessel. Thereafter, Phase D is added to the mixture of Phases A, B and C. Final adjustment (i.e. to achieve clarity) are then made. Glycerin should be added if the batch appears cloudy blue; water should be added if the batch appears to have a chromatic red color.

We claim:

1. A transparent oil-in-water gel emulsion composition for application to the lips or the facial area around the lips comprising:
    (a) an oil phase, containing at least one lipophilic solvent;
    (b) an aqueous phase containing at least one polyol; and
    (c) at least one sucrose ester emulsifier having an HLB from about 13 to about 16 selected from the group consisting of sucrose laurate, sucrose stearate, sucrose palmitate, sucrose oleate, sucrose myristate, sucrose cocoate, and sucrose isostearate wherein the at least one sucrose ester emulsifier is no more than 1.5% by weight of the total composition; and
    (d) a polymeric thickener selected from the group consisting of sclerotium gum, xanthan gum, sodium alginate, Carbomer, cellulose ethers, steareth-20 methyl acrylate copolymer, and $C_{10}$-$C_{30}$ alkyl acrylate crosspolymer
wherein the refractive index of the aqueous phase is about or less than +/−0.005 of that of the oil phase.

2. A composition according to claim 1, wherein the lipophilic solvent of the oil phase is selected from the group consisting of volatile silicone fluids, non-volatile silicone fluids, high molecular weight silicone polymers in the viscosity range of from about 60,000 centistokes to about 1,000,000 centistokes, liquid fatty alcohols having from 16 to 22 carbon atoms per molecule, volatile hydrocarbon fluids, esters and vegetable oils.

3. A composition according to claim 2, wherein the lipophilic solvent of the oil phase is a volatile silicone fluid.

4. A composition according to claim 3, wherein the volatile silicone fluid is selected from the group consisting of cyclopentasiloxane, cyclohexasiloxane and dimethicone.

5. A composition according to claim 2, wherein the lipophilic solvent of the oil phase is a volatile hydrocarbon fluid.

6. A composition according to claim 5 wherein the volatile hydrocarbon fluid is isododecane.

7. A composition according to claim 2 wherein the lipophilic solvent of the oil phase further comprises a lipophilic co-solvent selected from the group consisting of fatty acid esters and triglycerides.

8. A composition according to claim 1 wherein the polyol of the aqueous phase is selected from the group consisting of glycerin, polyethylene glycol, propylene glycol, polypropylene glycol, 1,3 butylene glycol, methylpropanediol, hexylene glycol and sorbitol.

9. A composition according to claim 1 wherein the molecular weight of the polyol is from about 300 to about 1,000 Daltons.

10. A composition according to claim 9 wherein the polyol is polyethylene glycol 400.

11. A composition according to claim 1 wherein the at least one sucrose ester emulsifier is sucrose laurate.

12. A composition according to claim 1 wherein the at least one sucrose ester fatty acid ester emulsifier is sucrose palmitate.

* * * * *